United States Patent [19]

Hetz

[11] Patent Number: 4,561,446
[45] Date of Patent: Dec. 31, 1985

[54] ULTRASONIC PROBE WHICH CAN BE INTRODUCED INTO A BODY

[75] Inventor: Walter Hetz, Erlangen, Fed. Rep. of Germany

[73] Assignee: Siemens Aktiengesellschaft, Berlin & Munich, Fed. Rep. of Germany

[21] Appl. No.: 433,377

[22] Filed: Oct. 8, 1982

[30] Foreign Application Priority Data

Oct. 15, 1981 [DE] Fed. Rep. of Germany ....... 3141022

[51] Int. Cl.$^4$ .............................................. A61B 10/00
[52] U.S. Cl. ........................................ 128/660; 128/7
[58] Field of Search ................................ 128/660–663, 128/4, 6–7

[56] References Cited

U.S. PATENT DOCUMENTS

| | | | |
|---|---|---|---|
| 3,942,530 | 3/1976 | Northered | 128/4 X |
| 4,176,661 | 12/1979 | Schubert et al. | 128/6 |
| 4,327,738 | 5/1982 | Green et al. | 128/660 |
| 4,336,794 | 6/1982 | Chikama | 128/4 |
| 4,401,123 | 8/1983 | Boba | 128/660 |
| 4,433,692 | 2/1984 | Boba | 128/660 |
| 4,489,728 | 12/1984 | Matsuo et al. | 128/4 X |

FOREIGN PATENT DOCUMENTS

| | | |
|---|---|---|
| 0039851 | 11/1981 | European Pat. Off. . |
| 2305501 | 4/1977 | Fed. Rep. of Germany . |
| 2950203 | 6/1980 | Fed. Rep. of Germany . |
| 3009482 | 9/1980 | Fed. Rep. of Germany . |

OTHER PUBLICATIONS

Boba, K., "UTS Wave Diagnostic Device with Endoscope", European Patent Application EP 0066185, Published 12/82.

Japanese Patent Application No. 5156746/1982, Laid Open 9/28/82.

Martin et al., "An Ultrasonic Catheter for Intravascular Measurement of Blood Flow: Technical Details", IEEE Transactions on Sonics and Ultrasonics, vol. SU-27, No. 6, Nov. 1980, pp. 277-286.

*Primary Examiner*—Kyle L. Howell
*Assistant Examiner*—Francis J. Jaworski
*Attorney, Agent, or Firm*—Hill, Van Santen, Steadman & Simpson

[57] ABSTRACT

An exemplary embodiment includes a probe tube at which an ultrasonic array is disposed. The aim of the disclosure is to construct an ultrasonic probe which, given an optimally small overall diameter, can particularly be employed for bladder endoscopy of male patients. The aim is inventively achieved in that an optical insert and an ultrasonic array are disposed in two layers radially offset and also offset relative to one another in the longitudinal direction of the tube, being disposed in such manner that the end face of the optical insert opening in front of the ultrasonic array in the direction toward the distal tube end only projects over the application surface (ultrasonic elements) of the ultrasonic array to such degree that, on the one hand, the space above the ultrasonic array can be sufficiently illuminated and, on the other hand, given a largely complete filling of the tube space below the ultrasonic array and optical insert with a bundle of the electrical connecting lines of the ultrasonic array proceeding in the direction of the proximal tube end, the overall diameter of the probe tube with an inserted or emplaced optical insert is optimally low for endoscopy purposes.

7 Claims, 4 Drawing Figures

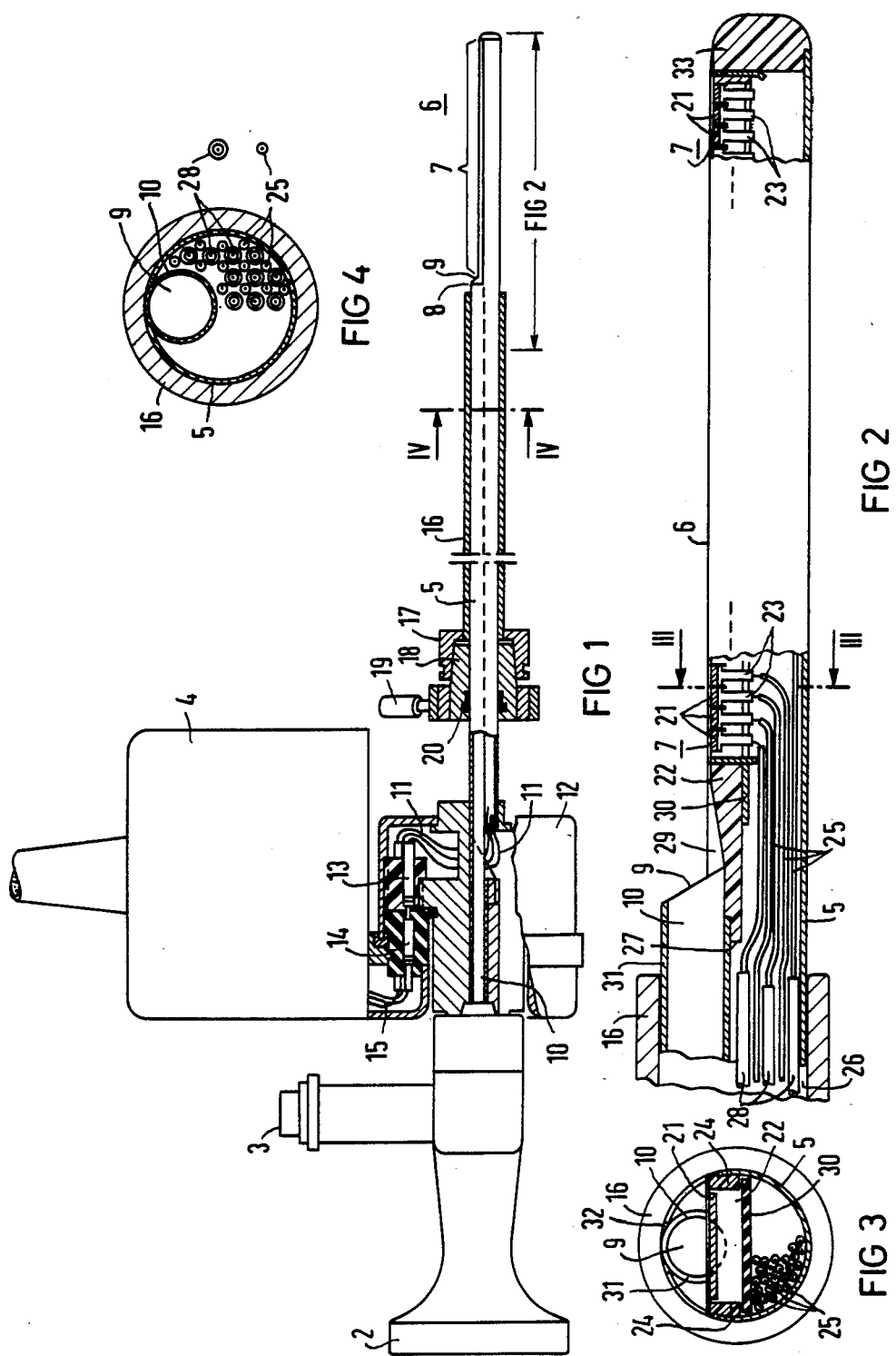

ULTRASONIC PROBE WHICH CAN BE INTRODUCED INTO A BODY

BACKGROUND OF THE INVENTION

The invention relates to an ultrasonic probe which can be introduced into a body, for example, into the body of a patient.

An ultrasonic probe of this type is known from the German LP No. 23 05 501. There is a desire to employ such ultrasonic probes in conjunction with endoscopy. In such a case, thus, the ultrasonic probe must be introduced into the body cavity of the patient at least in conjunction with an endoscopic optical insert. The endoscopic optical insert allows the physician to observe the examination location in the interior of the patient's body at which the ultrasonic probe is to be placed from the outside. When a suitable examination location has been found, then the ultrasonic applicator is placed in operation for the purpose of recording cross-sectional images. The type of scanning is as desired; thus, it can be a matter of a pure linear scan or a matter of an electronically generated sector scan. Likewise, a C-scan or the like is possible. An ultrasonic probe which is employed in conjunction with an optics insert in endoscopes is already known per se from the German OS No. 30 09 482. The ultrasonic transducer of this ultrasonic probe is a matter, however, of a mechanically pivoted ultrasonic head for sector scanning. Such a scanning head at most requires a signal line for the excitation and for the echo reception and a line for an angle generator. Apart from the drive wire or the drive shaft for the execution of the pivot motion of the acoustic head and apart from the angle generator, no space is required for further acoutrements of the ultrasonic transducer. For this reason, the ultrasonic transducer can be completely accomodated together with an optical insert in the probe tube which carries the transducer.

Such a structure is not possible without further ado given employment of an ultrasonic array. An ultrasonic array allows a larger-surface scanning of the examination subject, in particular of locations such as lie close to the array. Given a sector scanning, usable images only derive at a certain distance from the tip of the sector line field, i.e. from the acoustic head.

In order to be able to fully exploit the advantage of an ultrasonic array, the array should at least exhibit such a plurality of transducer elements that a usably resolved ultrasonic image with sufficient width is produced. Practice shows that usable images are supplied when the number of transducer elements lies at at least approximately 40 through 50 individual elements. This relatively high number of individual elements which can in turn be sub-divided (for example into two or, preferably, even more such as, for example, eight sub-transducers in the manner of the U.S. Pat. No. LP 4,305,014), however, requires a correspondingly high number of signal lines. As a rule, commercially available signal lines are relatively thick (they have a diameter in the range of $\phi = 0.6$ mm), since, for the purpose of mutual HF noise suppression, they are also provided with a HF protective jacket consisting, for example, of gold-plated copper wire in addition to the normal insulating layer consisting, for example, of Teflon.

SUMMARY OF THE INVENTION

The object of the present invention is to construct a probe tube for an ultrasonic array having a plurality of signal lines and an optical insert which, despite the additional optical insert and despite the fact that a multitude of lines must be conducted, has a small outside diameter. Thereby, the ultrasonic probe should particularly be employable in conjunction with endoscopy in standard endoscope guidance tubes. The dimensions should likewise be such that insertion into endoscope guidance tubes as are employed in urology for bladder examinations is possible. The probe tube and the optical insert should then fit in common into an endoscope guidance tube which, having the standard, maximally admitted dimensions, can be introduced without danger into the urinary bladder of a male patient through the urethra of the penis.

This object is inventively achieved with the characterizing features of patent claim 1.

The invention enables a particularly compact structure of a probe tube together with an optical insert. Thus, the desire for small dimensions is taken into consideration in an optimal manner; the objectives set forth are optimally resolved.

Further advantages and details of the invention derive from the following description of an exemplary embodiment on the basis of the accompanying drawing sheet in conjunction with the subclaims; and other objects, features and advantages will be apparent from this detailed disclosure and from the appended claims.

BRIEF DESCRIPTION OF THE DRAWING

FIG. 1 shows a commercially available endoscope for, for example, urological examinations, having a fitting optical insert and a probe tube designed to match it having an ultrasonic array;

FIG. 2 shows an enlarged detail of the distal end of the probe tube conducted in the endoscope guidance 2;

FIG. 3 shows a cross-section through the endoscope guidance tube, light waveguide insert, and probe tube at the location III—III of FIG. 2; and FIG. 4 shows the same cross-section at the location IV—IV of FIG. 1.

DETAILED DESCRIPTION

FIG. 1 shows an endoscope which is proximally equipped with an ocular 2, a cold light connection 3, and an electronics part 4 for the electrical signal servicing of an ultrasonic array and which is distally equipped with a probe tube 5. The probe tube 5, consisting of approximately 0.2 through 0.3 mm thick stainless steel, is flattened at its upper side at the outer-most distal end 6 (in that, for example, this end piece of the tube is designed stepped). The ultrasonic array 7 is seated on the flattened part of the end piece 6 of the tube. The, for example, slanted, distal end 9 of an optical insert 10 as is traditionally employed in endoscopy discharges at the location 8 at which the probe tube 5 merges into the flat part. The optical insert 10, which consists of an optics (not illustrated in greater detail) having fiber optical waveguides for cold light, is connected at the proximal end to the ocular 2 on the one hand, and, on the other hand, to the connection 3 for cold light. It proceeds parallel to the tube axis in the upperspace of the probe tube 5. The lower space of the probe tube, as is explained in greater detail on the basis of FIGS. 2 through 4, is filled in a particular manner with the signal lines of the ultrasonic array 7. The signal lines, which are indicated in FIG. 1 only as a proximally terminating bundle 11 in the composite piece 12 for the electronics part 4, are connected over appropriately designed contact plugs 13 at the proximal end to cooperating plug contacts 14 of the connecting lines 15 of the electronics part 4. The connector piece 12 has a metallic capsule housing. Accordingly, the electronics part 4 is also metallically encapsulated (for example, synthetic housing with inside metallization). Therefore, the electrical signal lines are electrically well-insulated toward the outside and are also well-protected against disruptive high frequency incursions from the outside.

In the standard manner, the endoscope of FIG. 1 also comprises an endoscope guidance tube 16. This guidance tube 16 is normally first introduced into the body cavity of the patient. Only subsequently is that part of the endoscope with which the inside of the body is to be examined introduced through the guidance tube 16. In the case of FIG. 1, thus, the guidance tube 16 is introduced, for example, through the urethra of the penis of the male patient up to the entry of the urinary bladder. Then, the probe tube 5 with the ultrasonic array 6 and the optical insert 10 is introduced into the bladder through the guidance tube 16. The probe tube 5 can be coupled to the endoscope tube 16. To this end, the endoscope guidance tube 16 exhibits a coupling shank 17 at its proximal end which meets with a coupling part 18 on the probe tube 5 having a locking lever 19. A sealing ring of the coupling piece is indicated with 20.

In the enlarged illustration of FIG. 2, the distal probe tube end 6 carries an ultrasonic array 7 with, for example, forty-eight ultrasonic elements 21 consisting of piezoelectric material which, as is standard, are applied on a damping body 22 consisting of, for example, synthetic resin with extenders. Each of the transducer elements 21 is divided in the manner of the U.S. Pat. No. 4,305,014 into, for example, four sub-transducer elements which are electrically connected to one another over common contact lugs 23. Finally, the distal ends of the signal lines of the proximal bundle 11 for the individual ultrasonic transducer elements are soldered onto the lower end of the contact lugs 23. At this location, the signal lines are only insulated; thus, they exhibit no additional high frequency (HF) shielding. Signal lines or signal line parts without additional HF insulation are referenced in FIGS. 2 through 4 with 25. Given the thus lower diameter (approximately 0.25 mm) of these signal lines or signal line parts 25, one succeeds in optimally filling the cavity remaining along the flattened, distallic end of the probe tube below the ultrasonic array with lines. A HF shielding of the lines only ensues in the space 26 behind the joint 27 between the ultrasonic array and the distal end of the optical insert 10. After this joint, precisely enough space is again present that shielded signal lines or signal line parts which are here specifically referenced with 28 and non-shielded signal lines or signal line parts which again bear the reference numeral 25 can be continued in mixed form in this space along the remaining part of the tube up to the connector piece 12 for the electronic part 4. This relationship is illustrated in the cross-section of FIG. 4 where non-shielded lines or line parts 25 come to lie so completely between shielded lines or line parts 28 that they are in turn shielded by the shielded lines or line parts 28.

In the enlarged detail of FIG. 2, the damping body 22 of the ultrasonic array 7 is proximally slanted at the abutting face relative to the end face 9 of the optical insert 10 in such manner that a slanted, planar trough 29 for the light exit of the optical insert derives there. In the cross-sectional illustration of FIG. 3, the components 24 are lateral pieces consisting of Araldit. The component 30 is a printed circuit board.

The following can also be derived from the cross-section illustration of FIG. 3.

The optical insert 10 is seated in a tube 31. Up to its transition to the flattened, distallic end part 6, i.e. up to the end face 9 of the optical insert 10, the probe tube 5 has the shape of a monobloc barrel. However, this monobloc barrel (or: literally, "full tube") exhibits a narrow slit 32 along its upper face parallel to the tube axis. This slit 32, which is indicated in FIG. 3, is selected in such manner that the inserted tube 31 for the optical insert 10 terminates flush toward the top with the circumference of the monobloc barrel through the slit. By so doing, one avoids having the wall thicknesses of the two tubes add up at the joint between the probe tube 5 and the tube 31 for the optical insert. The tube 31 for the optical insert, thus, can be slightly displaced toward the top, as a result of which more space again remains for the line guidance in the space 26 of the probe tube 5. Such a special design, thus, promotes the optimal matching between the interior accomodation of the probe tube and the outside diameter of said probe tube. When in contrast thereto, tubes 31 for the optical insert having a very thin wall thickness are employed, then the introduction of an opening slot 32 in the probe tube can be eliminated. In this case, the tube 31 for the optical insert merely presses against the inside wall of the outer probe tube 5. The wall thickness of both tubes add up in this case. Such an embodiment, of course, is also included under the invention. In FIG. 2, finally, the outer-most, distallic end of the flattened tube part 6 is provided with a casting resin closure 33.

In the exemplary embodiment of FIGS. 1 through 4, an optical insert 10 which is then closed in a cover tube 31 having an outer tube diameter of approximately 2.6 mm can be combined with a packet consisting of HF shielded or, respectively, intercalated, non-shielded connecting lines of an ultrasonic array having, for example, forty-eight transducer elements of the aforementioned type in such manner that the overall packet fits into a full probe tube 5 having an optimally low outside diameter of approximately 5.4 mm. A probe tube with such an outside diameter in turn is certain to fit into commercially available guide tubes for bladder endoscopy of male patients. Given a wall thickness of 0.8 mm, the outside diameter of said guide tube amounts to 21 Charrier this corresponding to 7 mm. The ultrasonic array itself is designed, for example, as a 7 Mhz array.

It will be apparent that many modifications and variations may be made without departing from the scope of the teachings and concepts of the present invention.

I claim as my invention:

1. Apparatus for the examination of a narrow body cavity, such as the bladder, comprising:
    (a) a guide tube dimensioned for insertion into said body cavity;
    (b) a probe tube having a longitudinal axis and a flat distal end portion, said probe tube having an inner surface, and an outer diameter for sliding into said guide tube;
    (c) a linear ultrasonic array disposed along said flat end portion of said probe tube;
    (d) an elongated optical insert for guiding light to said cavity and for receiving light reflected therefrom, said insert having a distal end; and
    (e) an additional tube disposed within said probe tube and attached to said inner surface thereof parallel to said longitudinal axis for removably receiving said optical insert in said additional tube with said end face of said optical insert disposed adjacent said ultrasonic array, said additional tube having an outer surface defining an open volume in combination with said inner surface of said probe tube; and (f) a plurality of electrical signal lines disposed in and extending along said open volume in said probe tube, said signal lines being adapted to connect said ultrasonic array to a processing means disposed outside said body cavity, wherein said optical insert illuminates said cavity after being inserted into said further tube.

2. Apparatus according to claim 1 wherein said distal end of said optical insert is disposed adjacent a proximal side of the ultrasonic array.

3. Apparatus according to claim 2 wherein said ultrasonic array is disposed at a distal end of said probe tube and further comprising an exterior surface overlying an active side of the ultrasonic array, said distal end of said optical insert projecting partially above said exterior surface.

4. Apparatus according to claim 2 wherein said guide tube has an outside diameter of about seven millimeters.

5. Apparatus according to claim 1 wherein said guide tube has an outside diameter of about seven millimeters.

6. Apparatus according to claim 5 wherein said ultrasonic array has at least about forty-eight transducer elements, and further comprising high frequency shielding applied to selected ones of said signal lines, and said high frequency shielding also shielding others of said signal lines which do not have high frequency shielding applied thereto.

7. Apparatus according to claim 1 wherein said probe tube has an outside diameter of approximately 5.4 millimeters.

* * * * *